United States Patent
Tegg et al.

(10) Patent No.: US 11,696,716 B2
(45) Date of Patent: Jul. 11, 2023

(54) NON-CONTACT ELECTRODE BASKET CATHETERS WITH IRRIGATION

(71) Applicant: St. Jude Medical, Atrial Fibrillation Division, Inc., St. Paul, MN (US)

(72) Inventors: Troy T. Tegg, Elk River, MN (US); Richard E. Stehr, Tucson, AZ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 816 days.

(21) Appl. No.: 15/155,277

(22) Filed: May 16, 2016

(65) Prior Publication Data
US 2016/0331254 A1    Nov. 17, 2016

Related U.S. Application Data

(63) Continuation of application No. 12/345,606, filed on Dec. 29, 2008, now Pat. No. 9,339,331.

(51) Int. Cl.
*A61B 18/14* (2006.01)
*A61B 5/00* (2006.01)
(Continued)

(52) U.S. Cl.
CPC ............ *A61B 5/283* (2021.01); *A61B 5/6858* (2013.01); *A61B 18/1492* (2013.01);
(Continued)

(58) Field of Classification Search
CPC .............. A61B 5/6858; A61B 18/1477; A61B 18/1492; A61B 2017/00867;
(Continued)

(56) References Cited

U.S. PATENT DOCUMENTS

| 4,522,212 A | 6/1985 | Gelinas et al. |
| 5,178,608 A | 1/1993 | Winters |

(Continued)

FOREIGN PATENT DOCUMENTS

| EP | 1442719 | 12/2003 |
| EP | 0889744 B1 | 1/2004 |

(Continued)

OTHER PUBLICATIONS

Communication pursuant to Article 94(3) EPC dated Jul. 11, 2014, 3 pages.

*Primary Examiner* — Quynh-Nhu H. Vu
(74) *Attorney, Agent, or Firm* — Kilpatrick Townsend & Stockton LLP

(57) ABSTRACT

Catheter systems and methods are disclosed. An exemplary catheter includes an outer tubing housing and an inner fluid delivery tubing, the inner fluid delivery tubing having at least one fluid delivery port. The catheter also includes a deployment member movable axially within the inner fluid delivery tubing. A plurality of splines are each connected at a proximal end to the outer tubing and at a distal end to deployment member. A seal is provided between the outer tubing and the inner fluid delivery tubing. A gasket is provided between the deployment member and the inner fluid delivery tubing. Both the seal and the gasket are configured to prevent blood or other fluid from ingressing into the outer tubing.

20 Claims, 9 Drawing Sheets

(51) Int. Cl.
*A61B 5/283* (2021.01)
*A61B 18/00* (2006.01)
*A61B 90/00* (2016.01)
*A61B 17/00* (2006.01)

(52) U.S. Cl.
CPC .............. *A61B 2017/00867* (2013.01); *A61B 2018/00214* (2013.01); *A61B 2018/00267* (2013.01); *A61B 2018/00351* (2013.01); *A61B 2018/00577* (2013.01); *A61B 2018/00642* (2013.01); *A61B 2018/00839* (2013.01); *A61B 2090/065* (2016.02); *A61B 2218/002* (2013.01); *C08L 2201/12* (2013.01)

(58) Field of Classification Search
CPC ........... A61B 2018/00214; A61B 2018/00267; A61B 2018/00351; A61B 2018/00577; A61B 2018/00839; A61B 2018/1465; A61B 2018/1467; A61B 2018/1475; A61B 2090/065; A61B 2218/002
See application file for complete search history.

(56) References Cited

U.S. PATENT DOCUMENTS

| | | | |
|---|---|---|---|
| 5,224,939 A | 7/1993 | Holman et al. | |
| 5,313,943 A * | 5/1994 | Houser | A61B 5/6858 600/374 |
| 5,380,301 A | 1/1995 | Prichard et al. | |
| 5,400,783 A | 3/1995 | Pomeranz et al. | |
| 5,456,254 A | 10/1995 | Pietroski et al. | |
| 5,542,928 A * | 8/1996 | Evans | A61B 18/082 604/113 |
| 5,626,136 A | 5/1997 | Webster, Jr. | |
| 5,628,313 A * | 5/1997 | Webster, Jr. | A61B 5/6858 600/374 |
| 5,647,870 A | 7/1997 | Kordis et al. | |
| 5,665,103 A * | 9/1997 | Lafontaine | A61B 5/06 606/198 |
| 5,680,860 A * | 10/1997 | Imran | A61B 18/1492 600/374 |
| 5,702,438 A | 12/1997 | Avitall | |
| 5,715,817 A | 2/1998 | Stevens-Wright et al. | |
| 5,715,832 A | 2/1998 | Koblish et al. | |
| 5,827,278 A | 10/1998 | Webster, Jr. | |
| 5,846,238 A * | 12/1998 | Jackson | A61N 1/056 606/41 |
| 5,855,552 A | 1/1999 | Houser et al. | |
| 5,871,483 A | 2/1999 | Jackson et al. | |
| 5,876,373 A | 3/1999 | Giba et al. | |
| 5,893,847 A | 4/1999 | Kordis | |
| 5,897,554 A * | 4/1999 | Chia | A61B 18/1492 606/41 |
| 5,925,038 A | 7/1999 | Panescu et al. | |
| 5,957,900 A * | 9/1999 | Ouchi | A61B 17/221 604/264 |
| 5,964,757 A | 10/1999 | Ponzi | |
| 6,029,091 A | 2/2000 | de la Rama et al. | |
| 6,071,282 A | 6/2000 | Fleischman | |
| 6,074,379 A | 6/2000 | Prichard | |
| 6,096,055 A | 8/2000 | Samson | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,231,543 B1 * | 5/2001 | Hegde | A61M 25/10 604/96.01 |
| 6,267,746 B1 | 7/2001 | Bumbalough | |
| 6,273,404 B1 | 8/2001 | Holman et al. | |
| 6,280,414 B1 | 8/2001 | Shah et al. | |
| 6,319,251 B1 | 11/2001 | Tu et al. | |
| 6,415,187 B1 | 7/2002 | Kuzma et al. | |
| 6,454,775 B1 | 9/2002 | Demarais et al. | |
| 6,491,681 B1 | 12/2002 | Kunis et al. | |
| 6,522,932 B1 | 2/2003 | Kuzma et al. | |
| 6,554,794 B1 | 4/2003 | Mueller et al. | |
| 6,652,515 B1 | 11/2003 | Maguire et al. | |
| 6,658,302 B1 | 12/2003 | Kuzma et al. | |
| 6,741,878 B2 | 5/2004 | Fuimaono et al. | |
| 6,748,255 B2 | 6/2004 | Fuimaono et al. | |
| 6,945,977 B2 | 10/2005 | Demarais et al. | |
| 6,961,602 B2 | 11/2005 | Fuimaono et al. | |
| 6,973,340 B2 | 12/2005 | Fuimaono et al. | |
| 7,004,937 B2 | 2/2006 | Lentz et al. | |
| 7,027,851 B2 | 4/2006 | Mejia | |
| 7,089,045 B2 | 8/2006 | Fuimaono et al. | |
| 7,099,712 B2 | 8/2006 | Fuimaono et al. | |
| 7,149,563 B2 | 12/2006 | Fuimaono et al. | |
| 7,214,220 B2 | 5/2007 | McGlinch et al. | |
| 7,217,256 B2 | 5/2007 | Di Palma | |
| 7,228,164 B2 | 6/2007 | Fuimaono et al. | |
| 7,257,434 B2 | 8/2007 | Fuimaono et al. | |
| 7,257,435 B2 | 8/2007 | Plaza | |
| 7,289,843 B2 | 10/2007 | Beatty et al. | |
| 7,412,274 B2 | 8/2008 | Mejia | |
| 7,429,261 B2 | 9/2008 | Kunis et al. | |
| 7,561,907 B2 | 7/2009 | Fuimaono et al. | |
| 7,608,063 B2 | 10/2009 | Le et al. | |
| 7,625,365 B2 | 12/2009 | McGlinch et al. | |
| 7,666,204 B2 | 2/2010 | Thornton et al. | |
| 7,959,601 B2 | 6/2011 | McDaniel et al. | |
| 7,985,215 B2 | 7/2011 | Guo et al. | |
| 8,103,327 B2 | 1/2012 | Harlev et al. | |
| 8,157,848 B2 | 4/2012 | Zhang et al. | |
| 8,221,390 B2 | 7/2012 | Pal et al. | |
| 8,273,016 B2 | 9/2012 | O'sullivan | |
| 8,333,732 B2 | 12/2012 | Fuimaono et al. | |
| 8,376,990 B2 | 2/2013 | Ponzi et al. | |
| 8,447,377 B2 | 5/2013 | Harlev et al. | |
| 8,486,063 B2 | 7/2013 | Werneth et al. | |
| 8,565,894 B2 | 10/2013 | Vetter et al. | |
| 8,603,069 B2 | 12/2013 | Selkie | |
| 8,608,703 B2 | 12/2013 | Riles et al. | |
| 8,700,120 B2 | 4/2014 | Koblish | |
| 8,744,599 B2 | 6/2014 | Tegg | |
| 8,755,861 B2 | 6/2014 | Harlev et al. | |
| 8,777,929 B2 | 7/2014 | Schneider et al. | |
| 8,814,824 B2 | 8/2014 | Kauphusman et al. | |
| 8,882,705 B2 | 11/2014 | McDaniel et al. | |
| 8,996,091 B2 | 3/2015 | de la Rama et al. | |
| 9,017,308 B2 | 4/2015 | Klisch et al. | |
| 9,247,990 B2 | 2/2016 | Kauphusman et al. | |
| 9,339,331 B2 | 5/2016 | Tegg et al. | |
| 9,433,751 B2 | 9/2016 | Ponzi et al. | |
| 9,468,495 B2 | 10/2016 | Kunis et al. | |
| 9,694,159 B2 | 7/2017 | Schneider et al. | |
| 10,034,637 B2 | 7/2018 | Harlev et al. | |
| 10,052,457 B2 | 8/2018 | Nguyen et al. | |
| 10,099,036 B2 | 10/2018 | Heideman et al. | |
| 11,272,886 B2 | 3/2022 | Harlev et al. | |
| 2002/0165484 A1 | 11/2002 | Bowe et al. | |
| 2003/0097094 A1 * | 5/2003 | Ouriel | A61F 2/013 604/93.01 |
| 2003/0114739 A1 | 6/2003 | Fuimaono et al. | |
| 2004/0133091 A1 | 7/2004 | Fuimaono et al. | |
| 2005/0159741 A1 | 7/2005 | Paul et al. | |
| 2006/0009690 A1 | 1/2006 | Fuimaono et al. | |
| 2007/0083194 A1 | 4/2007 | Kunis et al. | |
| 2007/0276212 A1 | 11/2007 | Fuimaono et al. | |
| 2008/0161801 A1 | 7/2008 | Steinke et al. | |
| 2009/0171274 A1 * | 7/2009 | Harlev | A61B 5/6859 604/95.04 |
| 2009/0192453 A1 | 7/2009 | Wesselmann | |
| 2009/0198300 A1 | 8/2009 | Zhang et al. | |
| 2012/0271302 A1 | 10/2012 | Behl et al. | |
| 2016/0213423 A1 | 7/2016 | Kauphusman et al. | |

FOREIGN PATENT DOCUMENTS

| | | |
|---|---|---|
| EP | 1254641 B1 | 11/2008 |
| EP | 1690564 B1 | 4/2009 |
| EP | 1723981 B1 | 8/2010 |

(56) References Cited

FOREIGN PATENT DOCUMENTS

| | | |
|---|---|---|
| EP | 2135634 B1 | 10/2011 |
| EP | 2018203 B1 | 6/2012 |
| EP | 1968679 B1 | 9/2016 |
| EP | 1759668 B1 | 12/2018 |
| EP | 2234537 B1 | 1/2019 |
| EP | 2155301 B1 | 4/2021 |
| JP | 4545384 B2 | 7/2010 |
| JP | 4887810 B2 | 2/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5944331 B2 | 7/2016 |
| WO | 9407412 A1 | 4/1994 |
| WO | 9843530 A1 | 10/1998 |
| WO | 0168178 A1 | 9/2001 |
| WO | 2004112629 | 6/2004 |
| WO | 2008091197 A1 | 7/2008 |

\* cited by examiner

NON-CONTACT ELECTRODE BASKET CATHETERS WITH IRRIGATION

CROSS-REFERENCE TO RELATED APPLICATIONS

This application is a continuation of U.S. application Ser. No. 12/345,606, filed 29 Dec. 2008, (the '606 application). The '606 application is hereby incorporated by reference as though fully set forth herein.

BACKGROUND OF THE INVENTION a. Field of the Invention

The instant invention is directed toward non-contact electrode basket catheters with irrigation for delivering a fluid (e.g., an anticoagulant) during a medical procedure. In particular, the non-contact electrode basket catheter of the present invention may be used to deliver the fluid between splines of the basket catheter during medical procedures.

b. Background Art

Normal heart rhythm is between 60 and 100 beats per minute. Tachycardia is a fast heart rate (usually over 100 beats per minute) caused by disease or injury. Tachycardias may begin in the upper chambers of the heart (the atria) or the lower chambers of the heart (the ventricles). Some tachycardias are harmless, but other tachycardias are life threatening. Tachycardias can deteriorate to fibrillation, a disorder in which, the heart does not move enough blood to meet the needs of the body.

Atrial fibrillation (AF) is the most common abnormal heart rhythm. It is a very fast, uncontrolled heart rhythm that occurs when the upper chambers of the heart (the atria) try to beat so fast (between 350 and 600 times per minute) that they only quiver. Ventricular fibrillation (VF) occurs when the lower chambers of the heart (the ventricles) produce fast and erratic electrical impulses that fail to induce synchronous mechanical contraction, such that oxygenated blood is not circulated through the body. Fibrillation in the ventricles is a life-threatening arrhythmia demanding immediate treatment.

Before a tachycardia deteriorates to fibrillation, various procedures may be used to treat the heart tissue and reduce or altogether eliminate the occurrence of fibrillations. It is well known that treatment benefits may be gained by creating lesions in the heart tissue, which change the electrical properties of the tissue, if the depth and location can be controlled. For example, cardiac ablation techniques are known for forming lesions at specific locations in cardiac tissue to lessen or eliminate undesirable atrial fibrillations. Likewise, biologic and chemical agents may be delivered into infracted tissue in the lower chambers of the heart (the ventricles) to promote angiogenesis for the treatment of Ventricular Tachycardia (VT). Other procedures are also known for treating these and other ailments. Use of a particular procedure depends at least to some extent on the desired treatment, and may also depend on other considerations, such as tissue characteristics.

A basket catheter may be employed for ablation and other procedures (e.g., mapping) on the heart. The catheter system may include an outer catheter shaft also referred to as a "guiding introducer". The guiding introducer defines at least one lumen or longitudinal channel. A delivery sheath is fitted through the guiding introducer. To pre-position the sheath at the appropriate location in the heart, a dilator is first fitted through the sheath. In an example of a procedure within the left atrium, the sheath and the dilator are first inserted in the femoral vein in the right leg. The sheath and dilator are then maneuvered up to the inferior vena cava and into the right atrium. In what is typically referred to as a transseptal approach, the dilator is pressed through the interatrial septum between the right and left atria. A dilator needle may be used here to make an opening for the dilator to pass through. The dilator expands the opening sufficiently so that the sheath may then be pressed through the opening to gain access to the left atrium and the pulmonary veins. With the sheath in position, the dilator is removed and the basket catheter, needle, or other device (depending on the procedure) is fed into the lumen of the sheath and pushed along the sheath into the left atrium. When positioned in the left atrium, various mapping and/or ablation procedures, such as the ablation procedures described above, may be performed within the heart.

Several difficulties may be encountered, however, during these medical procedures using some existing basket catheters. For example, a slowing or stoppage of the flow blood may occur between the splines of the basket catheter, e.g., where the splines are attached to the catheter. This slowing or stoppage of the flow of blood may result in blood clot formation and may possibly lead to a thrombus. A thrombus may decrease blood flow or even completely cut off blood flow, resulting in heart attack or stroke. Indeed, the risk of thrombus formation in the heart continues to exist even after the basket catheter has been removed following the medical procedure.

Thus, there remains a need for irrigation of a basket catheter during a medical procedure.

BRIEF SUMMARY OF THE INVENTION

It is desirable to be able to deliver an anticoagulant such as a heparinized saline solution or other fluid in a basket catheter during various medical procedures, e.g., to reduce the risk of blood clot or thrombus formation. One effective way to prevent blood coagulation and thrombus formation is to irrigate the electrode with heparinized saline. It is further desirable to be able to seal a distal end of the catheter to prevent blood ingress into the catheter shaft during the medical procedure.

These and other objectives can be accomplished by the catheter systems and methods disclosed herein by providing a non-contact electrode basket catheter with irrigation. A seal may also be configured in the catheter system to reduce or altogether prevent blood ingress into the catheter shaft.

An exemplary non-contact electrode basket catheter with irrigation includes an outer tubing housing an inner fluid delivery tubing, the inner fluid delivery tubing having at least one fluid delivery port. The catheter also includes a deployment member movable axially within the inner fluid delivery tubing. A plurality of splines are each connected at a proximal end to the outer tubing and at a distal end to deployment member. The plurality of splines expand when the deployment member is moved in a first direction, and the plurality of splines collapse when the deployment member is moved in a second direction, the first direction being opposite the second direction. A seal is provided between the outer tubing and the inner fluid delivery tubing. A gasket is provided between the deployment member and the inner fluid delivery tubing. Both the seal and the gasket are configured to prevent blood or other fluid from ingressing into the outer tubing.

An exemplary catheter system comprises a delivery sheath, and a non-contact electrode basket catheter insertable through the delivery shaft. The basket catheter includes a plurality of splines operable to be moved by a deployment member between a deployed position and an undeployed position. The basket catheter also includes a fluid delivery tube housed within the basket catheter. The fluid delivery tube has at least one fluid delivery port for irrigating within the basket catheter between the plurality of splines to reduce clotting or thrombus formation. The basket catheter also includes a seal fixedly provided between the fluid delivery tube and an outer tube of the basket catheter. The seal preventing blood or fluid ingress into the outer tubing.

Another exemplary non-contact electrode basket catheter system with irrigation comprises a catheter shaft, and a basket catheter insertable through the catheter shaft. The basket catheter includes a fluid delivery tubing provided within an outer tubing, and a plurality of splines connected to the outer tubing and on one end and to a deployment member on an opposite end. The deployment member is operable to move the splines between an expanded configuration and a collapsed configuration. The basket catheter also includes fluid delivery means for irrigating within the basket catheter between the plurality of splines to reduce clotting or thrombus formation. The basket catheter also includes sealing means for stopping blood or fluid from ingressing into the catheter shaft.

An exemplary method comprises the steps of moving a deployment member axially within an inner fluid delivery tubing in a first direction to expand a plurality of splines of a non-contact electrode basket catheter, and moving the deployment member axially within the inner fluid delivery tubing in a second direction to collapse the plurality of splines. The method also comprises the steps of irrigating between the splines of the non-contact electrode basket catheter, and preventing fluid ingress into a catheter shaft.

The foregoing and other aspects, features, details, utilities, and advantages of the present invention will be apparent from reading the following description and claims, and from reviewing the accompanying drawings.

BRIEF DESCRIPTION OF THE DRAWINGS

In FIG. 5b, the electrode traces are shown as the electrode traces may be fit into channels formed within interstitial spaces of the catheter shaft.

FIG. 6 is an isometric view of the basket catheter of FIG. 4 with an outer layer of the splines shown covering the electrodes and electrode traces in FIG. 5a.

DETAILED DESCRIPTION OF THE INVENTION

Several embodiments of a catheter system according to the present invention are depicted in the figures as the catheter system may be used for irrigation delivery of an anticoagulant, such as heparinized saline, or other fluid in a basket catheter during a medical procedure. In an exemplary embodiment, the basket catheter is a non-contact electrode basket catheter which may be used for ablation or other procedures (e.g., mapping). As described further below, the catheter of the present invention provides a number of advantages, including, for example, facilitating irrigation during the medical procedure to reduce blood clot or thrombus formation without blood ingress into the catheter shaft. The catheter system may also be used in difficult environments, such as in a beating heart.

Before continuing, it is noted that other components typical of catheter systems which are conventionally implemented for these and other medical procedures are not shown or described herein for purposes of brevity. Such components may nevertheless also be provided as part of, or for use with, the catheter system. For example, catheter systems commonly include or are used in conjunction with an ECG recording system, and/or various input and output devices. Such components are well understood in the medical devices arts and therefore further explanation is not necessary for a complete understanding of the invention.

Figure 1:
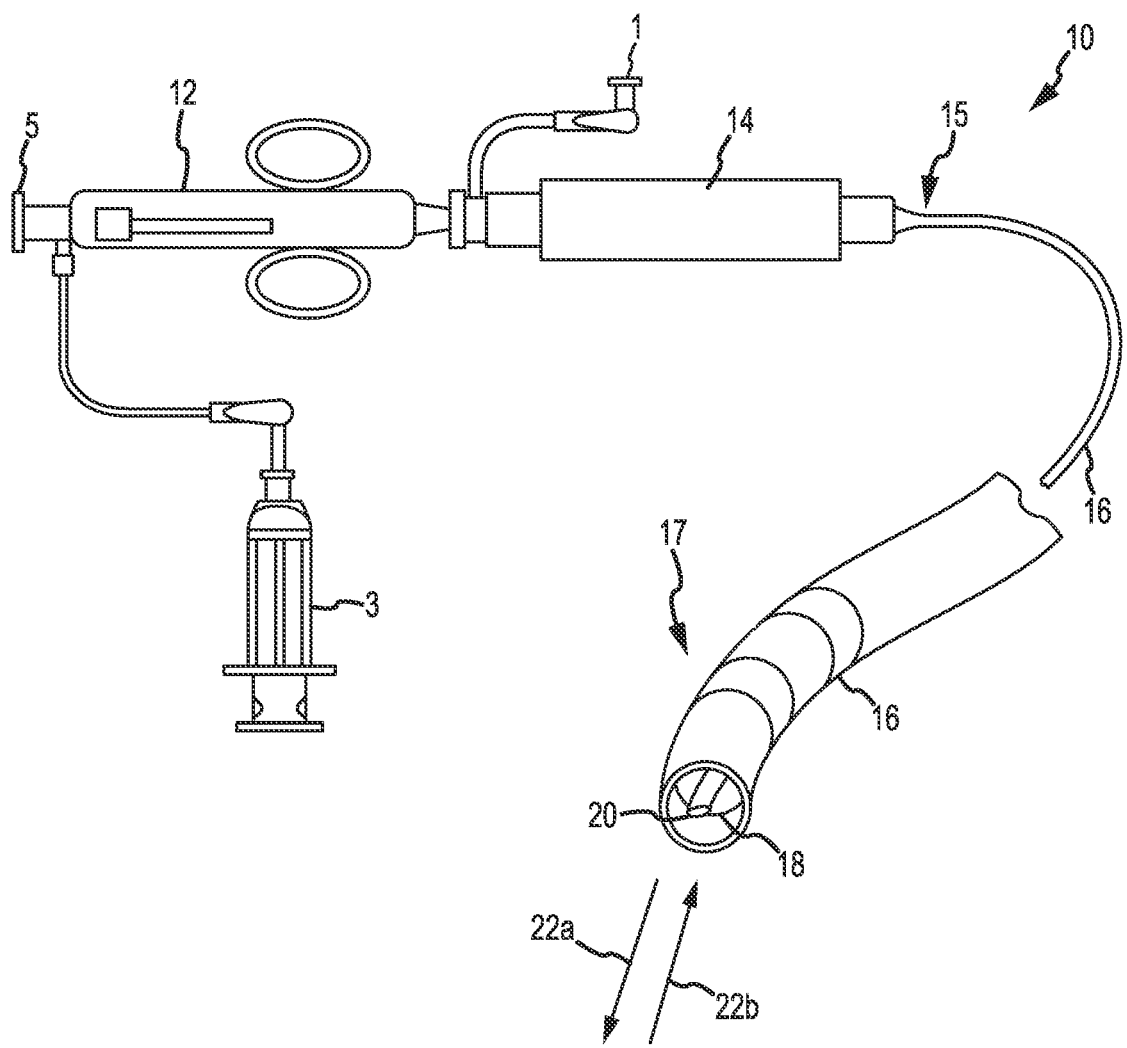
FIG. 1 is an isometric view of an exemplary embodiment of a catheter system.

FIG. 1 is an isometric view of an exemplary embodiment of a catheter system 10. The catheter system 10 may include a handle 12 and connector 14 at the base or proximal end 15. An outer catheter shaft also referred to as a "guiding introducer" 16 having a tubular body is connected to the connector 14 on the proximal end (e.g., illustrated by reference number 15 in FIG. 1) of the catheter system 10. As used herein and commonly used in the art, the term "proximal" is used generally to refer to components or portions of the catheter system 10, such as the handle 12 and connector 14 that are located or generally orientated away from or opposite the heart or other target tissue when the catheter system 10 is in use. On the other hand, the term "distal" (e.g., illustrated in FIG. 1 by reference number 17) is used generally to refer to components located or generally orientated toward the heart or other target tissue when the catheter system 10 is in use.

The guiding introducer 16 defines at least one lumen or longitudinal channel. A delivery sheath 18 is fitted through the guiding introducer 16. In one implementation, the guiding introducer 16 and sheath 18 are fabricated from a flexible resilient material, and are preferably fabricated of materials suitable for use in humans, such as nonconductive polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials. Some portions of the guiding introducer 16 and/or sheath 18 may be braided for enhanced stiffness.

In exemplary implementations, the guiding introducer 16 and sheath 18 are each about two to four feet long, so that they may extend from the left atrium through the body and out of the femoral vein in the right leg and be connected with various catheter devices such as the connector 14, one or more fluid control valves 1-3, and the like.

The sheath 18 is configured to receive and guide a device for carrying out the procedure (e.g., the basket catheter 25 shown in FIG. 2a-b) within the lumen to the target tissue. The sheath 18 is pre-positioned in the appropriate location in the heart prior to introduce a device. To pre-position the sheath 18 at the appropriate location in the heart, a dilator 20 is first fitted through the sheath 18. In an example of a procedure within the left atrium, the sheath 18 and the dilator 20 are first inserted in the femoral vein in the right leg. The sheath 18 and dilator 20 are then maneuvered up to the inferior vena cava and into the right atrium. In what is typically referred to as a transseptal approach, the dilator 20 is pressed through the interatrial septum between the right and left atria. A needle may be used here to make an opening for the dilator 20 to pass through. The dilator expands the opening sufficiently so that the sheath 18 may then be pressed through the opening to gain access to the left atrium and the pulmonary veins. With the sheath 18 in position, the dilator 20 is removed and the basket catheter 25 (FIG. 2a-b) may be fed into the lumen of the sheath 18 and pushed along the sheath 18 into the left atrium. When positioned in the left atrium, various procedures (e.g., ablation and mapping procedures) may be performed within the heart tissue using the basket catheter.

Figure 2A:
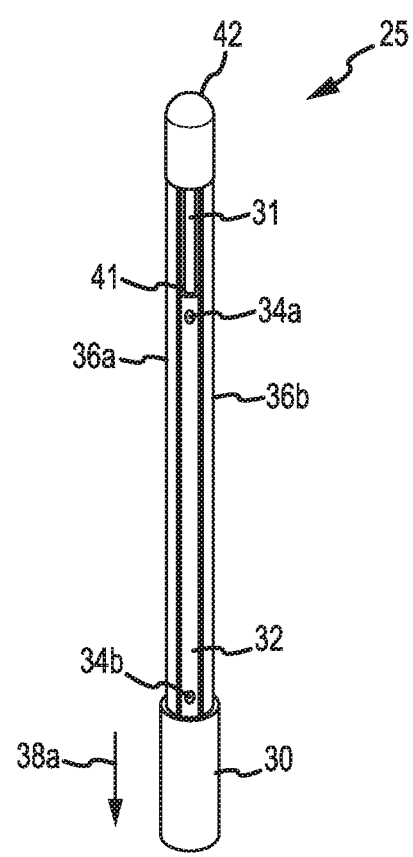
FIG. 2a-b are isometric views of an exemplary embodiment of a non-contact electrode basket catheter with irrigation which may be implemented with the catheter system in FIG. 1, wherein (a) shows the basket portion of the catheter in a collapsed configuration, and (b) shows the basket portion of the catheter in an expanded configuration.
Figure 2B:
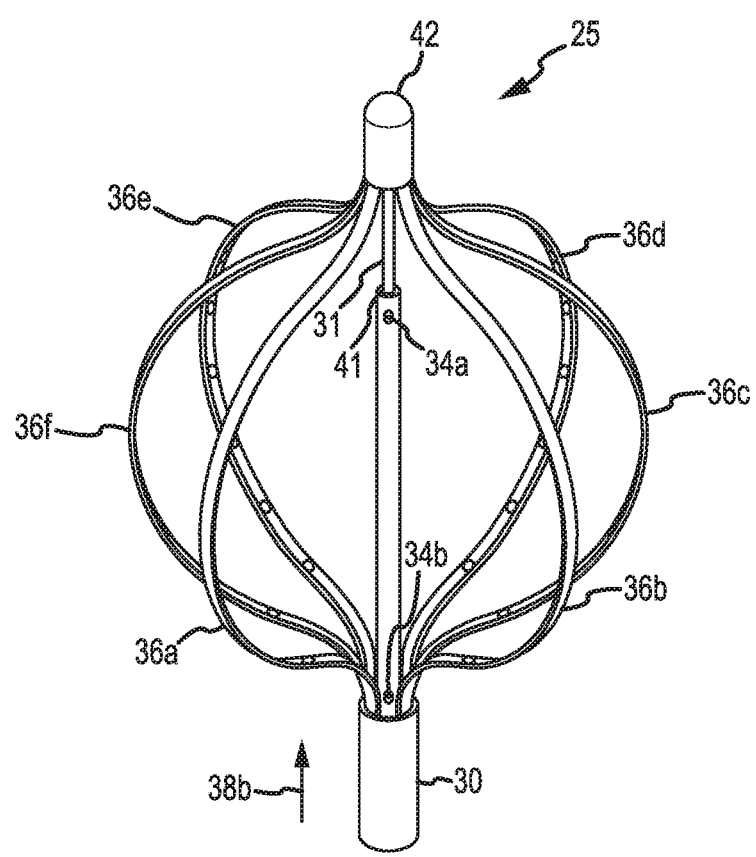

Once the sheath 18 is pre-positioned in the appropriate location in the heart, the basket catheter 25 may be at least partially extended out from the lumen at the distal end 17 of the sheath 18 (e.g., in the direction illustrated by arrow 22a) so that the basket catheter 25 may be positioned adjacent the target tissue, and then expanded as illustrated in FIG. 2b for the medical procedure. The basket catheter 25 may also be collapsed as illustrated in FIG. 2a, and then retracted (e.g., in the direction of arrow 22b) before removing the catheter system 10 from the body.

Before continuing, it is noted that the catheter system 10 has been described as it may be inserted for procedures in the left atrium in the vicinity of or within the pulmonary veins of the heart. The catheter system 10, however, is not limited to such procedures, and may be used for procedures involving other target tissue in other areas of the heart and body.

The following discussion will now be with reference to the basket catheter 25 shown in FIG. 2a-b. FIG. 2a-b are isometric views of an exemplary embodiment of a non-contact electrode basket catheter 25 with irrigation which may be implemented with the catheter system 10 in FIG. 1, wherein (a) shows the basket portion of the catheter in a collapsed configuration, and (b) shows the basket portion of the catheter in an expanded configuration.

In these figures, an exemplary basket catheter 25 is shown as it may include an outer tubing 30 housing an inner fluid delivery tubing 32 and a deployment member 31. The inner fluid delivery tubing 32 includes at least one fluid delivery port 34 within the splines 36 of basket catheter 25. It is noted that two fluid delivery ports 34a-b and splines 36a-b are visible in FIG. 2a. In FIG. 2b, splines 36a-f are visible in FIG. 2b. However, the basket cathether 25 is not limited to any particular configuration (including number of splines or number or placement of ports), as will be readily understood by those having ordinary skill in the art after becoming familiar with the teachings herein.

Each spline 36 is connected at the proximal end of the splines 36 to the outer tubing 30, and each spline 36 is connected at the opposite or distal end of the splines 36 to the deployment member 31. The deployment member 31 is operable to be moved in a first direction (e.g., in the direction of arrow 38a) relative to the outer tubing 30 to expand the splines 36 to a deployed position, as shown in FIG. 2b. The deployment member 31 is also operable to be moved in a second direction (e.g., in the direction of arrow 38b in FIG. 2b) relative to the outer tubing 30 to collapse the splines 36 to an undeployed position, as shown in FIG. 2a.

The deployment member 31 may include a pull wire. For example. The deployment member 31 may be a solid stainless steel or Nitinol wire. Alternatively, the deployment member 31 may be a hollow tubing (or configured to house tubing). An embodiment wherein the deployment member 31 is a fluid delivery tubing is described in more detail below with reference to FIG. 3b. In either case, however, the deployment member 31 should be manufactured to be sufficiently stiff such that the deployment member 31 can be operated remotely (e.g., outside of the patient's body) to be moved in the directions illustrated by arrow 38a and 38b in FIG. 2a-b to expand and contract the splines 36.

In any event, the basket catheter 25 may be inserted into the catheter shaft (e.g., sheath 18) in its undeployed position as shown in FIG. 2a for placement in the patient's body (e.g., within a heart chamber). The basket catheter 25 may then be expanded to its deployed position as shown in FIG. 2b for a medical procedure within the patient's body. Following the procedure, the basket catheter 25 may again be collapsed to its undeployed position so that the basket catheter 25 may be withdrawn through the delivery sheath 18 of the catheter 10.

In an exemplary embodiment, the deployment member 31 may be connected to port 5 on the handle 12 of catheter system 10 (in FIG. 1). A handle portion may be operatively associated with the deployment member 31 in such a manner that movement of the handle is directly translated into movement of the deployment member 31. Other embodiments of deployment systems are also contemplated and are not limited to the specific implementation described above. For example, the handle may be spring-loaded (not shown). The spring acts to bias the handle in a fully extended or pulled back position. Accordingly, a force must be applied to the handle in order to release the handle, and hence return the deployment member 31 toward its starting position. This may help ensure that the user does not leave the splines 36 of the basket in the expanded position as shown in FIG. 2b when attempting to remove the basket catheter 25 from the patient's body. This may also help ensure that the basket catheter 25 is not accidentally deployed during placement in the patient's body (doing so could cause unintended damage to tissue or other parts of the patient's body). Still other embodiments are also contemplated. For example, different mechanisms for controlling the distance the deployment member 31 can travel may also be implemented.

Figure 3A:
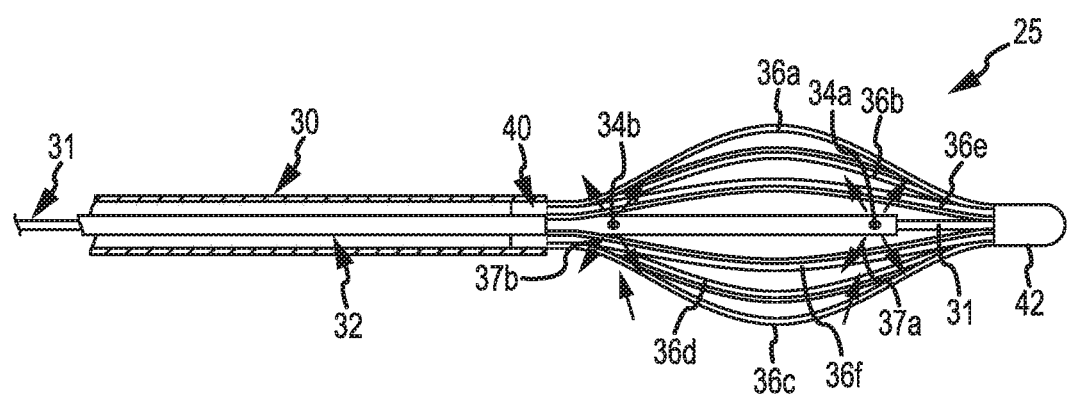
FIG. 3a is a cutaway isometric view of a distal portion of the basket catheter showing an exemplary configuration of distal fluid delivery ports.

FIG. 3a is cut-away isometric view of a distal portion of the basket catheter 25 showing an exemplary configuration of distal fluid delivery ports 34. Fluid delivery is illustrated by arrows 37a as the fluid may be delivered from ports 34a at the distal end of the fluid delivery tube 32, and by arrows 37b from ports 34a as the fluid may be delivered from ports 34b at the proximal end of the fluid delivery tube 32.

A seal 40 is also visible in FIG. 3a. The seal 40 may be manufactured of any suitable material. Seal 40 is provided between the inner fluid delivery tube 32 and the outer tubing 30. For example, the seal 40 may be molded or bonded to the inner fluid delivery tube 32 and/or the outer tubing 30. In an exemplary embodiment, the seal 40 may be oversized, e.g., having an inner diameter which is smaller than the outer diameter of the inner fluid delivery tubing 32 and having an outer diameter which is larger than the inner diameter of the outer tubing 30. The specific diameters may vary depending on a number of design considerations, such as, the diameters of the inner fluid delivery tubing 32 and outer tubing 30, or other components of the catheter 10. Sizing the diameters in such a manner enables the seal 40 to provide a snug fit between the tubing 30 and 32 to prevent blood or other fluid from ingressing back within the catheter shaft.

It should also be noted that blood or other fluid may also be kept from ingressing back within the catheter shaft through the fluid delivery ports 34a and 34b by continuous fluid delivery at a positive pressure through these ports. In exemplary embodiments, it has been determined that fluid flow rates of 1 mL/m to 5 mL/m provide sufficient positive pressure so as to prevent blood or other fluid from ingressing through the fluid delivery ports 34a and 34b. However, these are merely exemplary, and specific flow rates may be determined for any of a wide variety of fluid delivery port configurations by those having ordinarly skill in the art after becoming familiar with the teachings herein.

A gasket 41 is visible in FIGS. 2a and 2b, and serves a similar purpose to the seal 40 in FIG. 3a. Specifically, the gasket 41 enables the deployment member 31 to be moved in the directions illustrated by arrows 38a and 38b to expand and collapse the splines 36, while preventing blood or other fluid from ingressing back within the catheter shaft.

In an exemplary embodiment, the seal 40 and gasket 41 may be manufactured of an elastic polymer. However, the seal 40 and gasket 41 may be manufactured of any other suitable material as well, including but not limited to rubber, plastic, or metal.

Figure 3B:
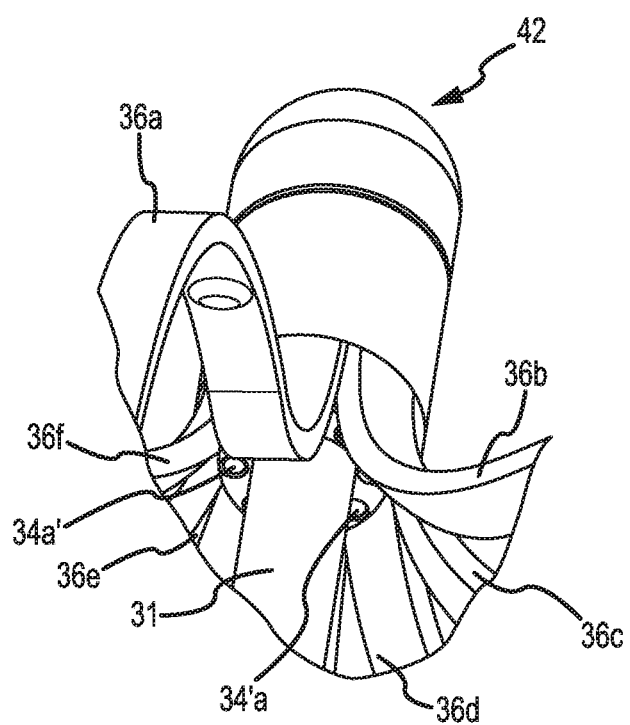
FIG. 3b is a close-up isometric view of a distal portion of the basket catheter showing an alternative configuration of the distal fluid delivery ports.

FIG. 3b is a close-up isometric view of a distal portion 42 of the basket catheter 25 showing an alternative configuration of the distal fluid delivery ports 34a'. In this embodiment, the deployment member 31 may be a tubing (or house a tubing) fluidically connected on one end to a fluid source, and on the other end to the distal fluid delivery ports 34a' provided on the deployment member 31. The distal fluid delivery ports 34a' may be fluidically connected to the same fluid source as the inner fluid delivery tubing 32 or to a separate fluid source. In any case, such an embodiment enables fluid delivery closer to the distal portion 42 of the basket catheter 25 even when the splines 36 are in an undeployed position (e.g., FIG. 2a).

Before continuing, it is noted that any configuration of the distal fluid delivery ports 34a' may be implemented and is not limited to the configuration (or number of ports) shown in FIG. 3b. Likewise, distal fluid delivery ports 34a' may be implemented with (in addition to) or without the fluid delivery ports 34a on inner fluid delivery tubing 32.

Figure 4:
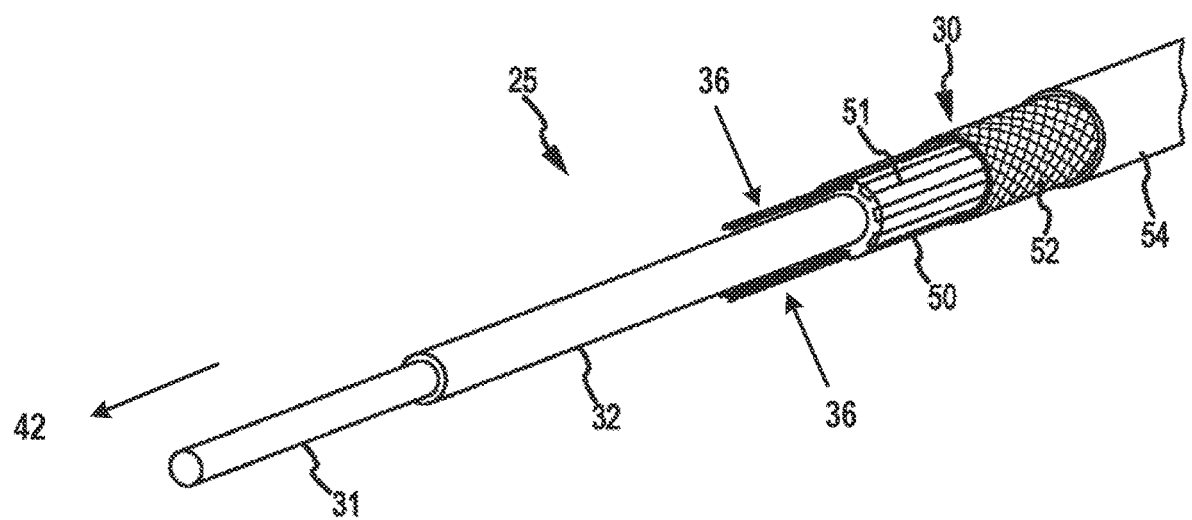
FIG. 4 is an isometric view of an exemplary basket catheter without the splines.

Although the fluid delivery mechanisms and irrigation systems and methods described above may be implemented with any suitable basket catheter 25, exemplary manufacture of a preferred embodiment of a non-contact electrode basket catheter will now be described with reference to FIG. 4-6. FIG. 4 is an isometric view of an exemplary basket catheter 25 without the splines 36. In FIG. 4, the deployment member 31 is shown fitted within fluid delivery tubing 32. The deployment member 31 may be a Nitinol wire which may be pre-bent to the desired shape. The deployment member 31 is configured for axial movement relative to the fluid delivery tubing 32. The fluid delivery tubing 32 is in turn fitted within outer tube 30. Outer tube 30 may comprise an inner shaft 50 which provides structural support and also has formed therein channels or interstitial spaces 51 for electrical wiring and/or fluid tubing (see, e.g., FIG. 5b). Outer tube 30 may also comprise a braided section 52 to contain the electrical wiring and/or fluid tubing within the interstitial spaces 51, and a cover 54.

It should be noted that although the section of the basket catheter 25 shown in FIG. 4 is depicted as having a circular cross-section, the cross-section may intentionally or unintentionally have a wide variety of cross-sectional configurations, and need not be circular. For example, manufacturing irregularities may result in different cross-sectional configurations. Or for example, different cross-sectional configurations (e.g., hexagonal, octagonal) may be intentionally selected to achieve desired properties. The particular configuration used will depend at least to some extent on design considerations. Exemplary design considerations may include, but are not limited to, the material and desired structural properties, the length, shape, and cross-sectional area. And of course, the design parameters may be different for various procedures or physician preferences.

Figure 5A:
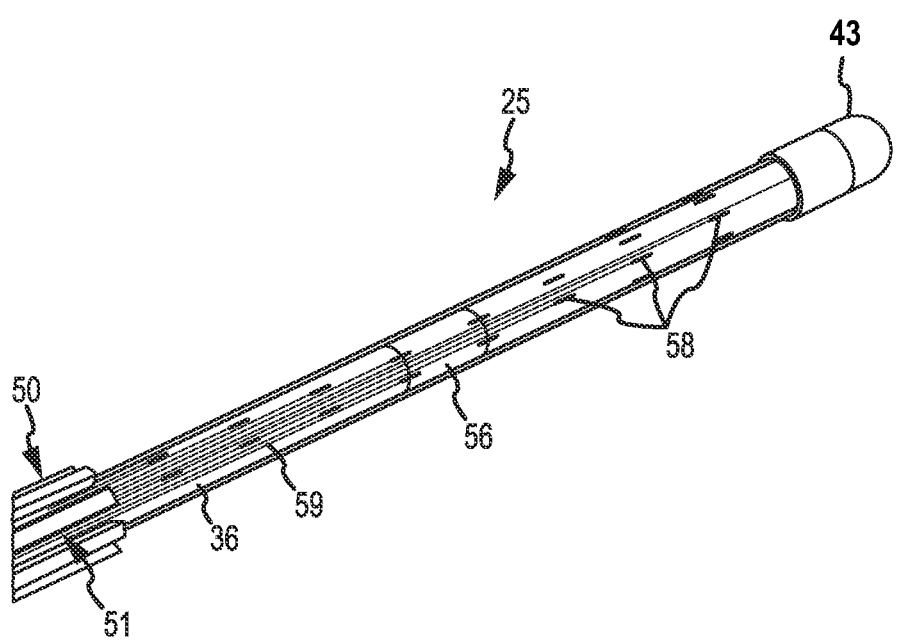
FIG. 5a-b are isometric views of the basket catheter of FIG. 4 with the base layer of the splines attached to show electrodes and electrode traces for the basket catheter.
Figure 5B:
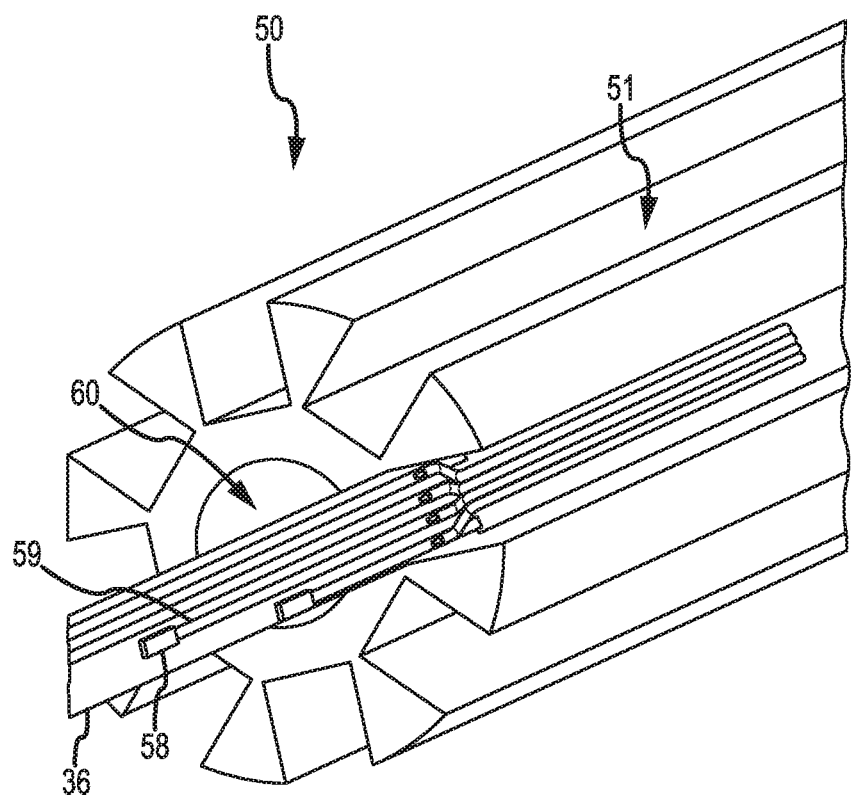

FIG. 5a-b are isometric views of the basket catheter 25 of FIG. 4 with the base layer 56 of the splines 36 attached to show electrodes 58 and electrode traces 59 for the basket catheter. In an exemplary embodiment, the splines 36 are formed from sheets. The sheets can be formed of a suitable flexible material such as plastic (e.g., polyimide). Plastic-coated stainless steel sheets may also be used to provide additional rigidity. In any event, the sheets are formed with a plurality of longitudinally extending slits spaced transversely of the sheet. Longitudinally spaced apart electrodes 58 and corresponding electrode traces 59 are provided on the splines 36.

The splines 36 may be formed by rolling the sheets onto a mandrel and then bonding the distal ends to the distal end 43 of the deployment member 31, and on the proximal end to the outer tube 30, e.g., within the channels 51. The sheets form a flexible circuit and may include gold plated electrode tabs 58.

In FIG. 5b, the electrode traces are shown as the electrode traces may be bonded so that the electrode traces 59 fit through the channels 51 of the outer tube 32. The traces 59 may then be connected to electrical wiring and extend through the lumen of the catheter system 10. The electrical wiring may convey electrical signals between the electrodes 58 and one or more control system (not shown). For example, the electrical signals may be used to control output of ablation electrodes, or for processing input from mapping electrodes for viewing by the user, (e.g., on an electrical monitoring device).

It is also noted that the fluid delivery tubing 32 may also extend through a channel 60 formed through the center of the outer tube 30. Of course other designs for the inner shaft 50 of the outer tube 30 may also be implemented, as will be readily understood by those having ordinary skill in the art after becoming familiar with the teachings herein. For example the channel 60 need not maintain the inner fluid delivery tubing 32 in the center of outer tube 30. It is only desired that the inner fluid delivery tubing 32 be maintained in a substantially constant position within the diameter of the outer tube 30 for uninterrupted flow of the fluid during the procedure.

Figure 6:
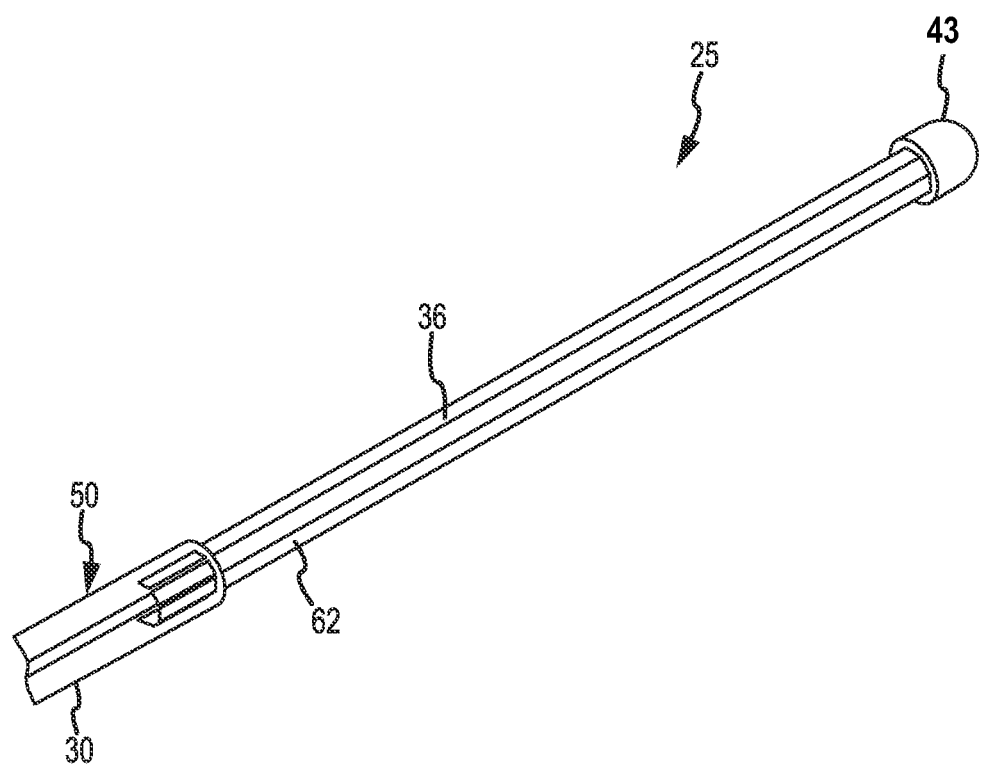

FIG. 6 is an isometric view of the basket catheter 25 of FIG. 4 with an outer layer 62 of the splines 36 shown covering the electrodes 58 and electrode traces 59 in FIG. 5a. Accordingly, the splines 36 may form a non-contact electrode basket catheter. The outer layer 62 may also be used as an additional stiffener to protect the flexible circuit portion of the splines 36.

It is noted that the various embodiments of catheter system 10 described above may also be implemented with a wide variety of different sensing means. These sensing means enable the catheter system 10 to be implemented for tissue contact assessment during the procedures, including contact with the tissue. For example, the catheter system 10 may include one or more piezoelectric sensor embedded in the splines 36. The piezoelectric sensor generates electric signals in response to stresses caused by contact with the tissue. Radiopaque sensors may also be used. Still other exemplary sensing devices may include pressure, thermistor, thermocouple, or ultrasound sensors. In addition, more than one sensor or type of sensor may be implemented to provide additional feedback to the user. In any event, when the splines 36 are positioned in contact with and/or moved over a tissue, the sensors may be implemented to generate an electrical signal corresponding to stress caused by this contact and/or movement for tissue contact assessment.

It is noted that any suitable analog and/or digital device may also be implemented for outputting data of electrical signals generated by the sensor(s) to a user. In addition, the electrical signals may be further characterized using a suitable processing device such as, but not limited to, a desktop or laptop computer. Such processing device may be implemented to receive the voltage signal generated by the contact assessment sensor(s) and convert it to a corresponding contact condition and output for the user, e.g., at a display device, an audio signal, or tactile feedback or vibrations on the handle of the catheter. In any event, circuitry for conveying output of the piezoelectric sensor to a user in one form or another may be readily provided by those having ordinary skill in the electronics arts after becoming familiar with the teachings herein.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly described. Changes in detail or structure, such as but not limited to combinations of various aspects of the disclosed embodiments, may be made without departing from the spirit of the invention as defined in the appended claims.

What is claimed is:

1. A catheter, comprising:
    an outer tubing that forms an outer surface of the catheter, wherein the outer tubing comprises an outer cover and an inner shaft disposed within the outer cover, wherein the inner shaft comprises a plurality of inner shaft channels that extend along a length of the inner shaft; and
    a plurality of splines configured to deploy from an undeployed configuration to an expanded configuration, wherein a proximal end of each of the plurality of splines is connected to a distal end of the outer tubing and is disposed within a respective one of the plurality of inner shaft channels to prevent relative movement between the proximal end of each of the plurality of splines and the distal end of the outer tubing, wherein each of the plurality of splines comprises a flexible circuit that extends along a length of the spline, electrodes that are distributed along the spline, and an outer layer that covers the electrodes to prevent direct contact between the electrodes and myocardial tissue within a cardiac muscle during at least one of a therapy and diagnostic procedure, wherein the outer layer is configured to structurally stiffen the spline,
    wherein the catheter is configured to be inserted into and advanced through a lumen of a separate introducer sheath.

2. The catheter of claim 1, wherein the electrodes are configured for use in conducting one or more of: anatomy mapping, electrophysiological mapping, temperature measuring, cardiac pacing, or myocardial tissue ablation.

3. The catheter of claim 2, wherein the electrodes comprise gold plated electrodes.

4. The catheter of claim 1, further comprising electrical leads that extend through at least one of the plurality of inner shaft channels and the outer tubing, wherein the electrical leads communicatively couple at least a plurality of electrodes to controller circuitry.

5. The catheter of claim 1, further comprising an inner fluid delivery tubing within the outer tubing, and a deployment member axially movable within the inner fluid delivery tubing; wherein:
    a distal end of the deployment member is coupled to a distal end of the plurality of splines; and
    the plurality of splines is configured to expand axially outward in response to movement of the deployment member in a first direction, and collapse axially inward in response to movement of the deployment member in a second direction, the second direction being opposite the first direction.

6. The catheter of claim 1, further comprising:
    an inner fluid delivery tubing within the outer tubing;
    a deployment member;
    a seal disposed between the outer tubing and the inner fluid delivery tubing; and
    a gasket disposed at an end of the inner fluid delivery tubing between the deployment member and the inner fluid delivery tubing, wherein both the seal and the gasket are configured to prevent blood or other fluid from ingressing into the outer tubing and the inner fluid delivery tubing.

7. The catheter of claim 6, wherein the seal is maintained in a fixed position relative to the outer tubing and the inner fluid delivery tubing.

8. The catheter of claim 6, wherein the seal has an inner diameter smaller than an outer diameter of the inner fluid delivery tubing, and wherein the seal has an outer diameter larger than an inner diameter of the outer tubing.

9. The catheter of claim 6, wherein:
    the deployment member is axially movable within the inner fluid delivery tubing;
    a distal end of the deployment member connected to each of the plurality of splines; and
    the deployment member extends through the gasket and is configured to be moveable through the gasket to expand and collapse the plurality of splines.

10. The catheter of claim 1, further comprising an inner fluid delivery tubing and a deployment member, wherein the deployment member extends within the inner fluid delivery tubing.

11. The catheter of claim 1, wherein distal ends of the plurality of splines are anchored to one another, and proximal ends of the plurality of splines are anchored by the outer tubing, thereby forming an orb shape as the plurality of splines are deployed in the expanded configuration.

12. The catheter of claim 1, wherein the proximal end of each of the plurality of splines is directly connected to the distal end of the outer tubing.

13. A catheter comprising:
    a catheter shaft that forms an outer surface of the catheter, wherein the catheter shaft comprises an outer cover and an inner shaft that extends within the outer cover, wherein the inner shaft comprises a plurality of inner shaft channels that extend along a length of the inner shaft;
    an expandable structure coupled to a distal end of the catheter shaft, wherein the expandable structure comprises a plurality of splines, wherein a proximal end of each of the plurality of splines is connected to a distal end of the catheter shaft and is disposed within a respective one of the plurality of inner shaft channels to prevent relative movement between the proximal end of each of the plurality of splines and the distal end of the catheter shaft, wherein each of the plurality of splines comprises a flexible circuit that extends along a length of the spline, electrodes that are distributed along the spline, and an outer layer that covers the electrodes, wherein the outer layer is configured to prevent direct contact between the electrodes and tissue during at least one of a therapy and diagnostic procedure;

an inner deliver tubing comprising a plurality of fluid delivery ports, wherein the plurality of fluid delivery ports is configured to direct irrigation fluid toward the expandable structure;

a fluid delivery lumen extending along a length of the catheter shaft and coupled to the plurality of fluid delivery ports, wherein the fluid delivery lumen is configured to distribute fluid from a reservoir disposed at a proximal end of the catheter shaft to the plurality of fluid delivery ports; and a deployment member that extends within the fluid delivery lumen, wherein a distal end of the deployment member is connected to a distal end of each of the plurality of splines, wherein the deployment member is axially movable within the catheter shaft to reconfigure the plurality of splines between an undeployed configuration and an expanded configuration, wherein the catheter is configured to be inserted into and advanced through a lumen of a separate introducer sheath.

14. The catheter of claim 13, wherein the electrodes are configured to conduct one or more of: anatomy mapping, electrophysiological mapping, temperature measuring, cardiac pacing, or myocardial tissue ablation.

15. The catheter of claim 14, wherein the outer layer is configured to structurally stiffen the-expandable structure in the expanded configuration.

16. The catheter of claim 14, wherein the electrodes comprise gold plated electrodes.

17. The catheter of claim 13, further comprising a handle and electrical leads, wherein the electrical leads extend through at least one of the plurality of inner shaft channels and the catheter shaft, wherein the electrical leads communicatively couple the electrodes to the handle.

18. The catheter of claim 13, wherein the plurality of fluid delivery ports is circumferentially disposed around the fluid delivery lumen.

19. The catheter of claim 13, wherein the electrodes are configured-for use in conducting one or more of: anatomy mapping, electrophysiological mapping, temperature measuring, cardiac pacing, or myocardial tissue ablation.

20. The catheter of claim 13, wherein the proximal end of each of the plurality of splines is directly connected to the distal end of the catheter shaft.

\* \* \* \* \*